US00RE38018E

(19) United States
(12) Reissued Patent
Anctil et al.

(10) Patent Number: US RE38,018 E
(45) Date of Reissued Patent: Mar. 4, 2003

(54) ANGLED ROTARY TISSUE CUTTING INSTRUMENT AND METHOD OF FABRICATING THE SAME

(75) Inventors: Stephanie B. Anctil, Jacksonville, FL (US); Gary Peters, Jacksonville, FL (US)

(73) Assignee: Medtronic Xomed, Inc., Jacksonville, FL (US)

(21) Appl. No.: 09/799,898

(22) Filed: Mar. 7, 2001

Related U.S. Patent Documents

Reissue of:
(64) Patent No.: 5,922,003
Issued: Jul. 13, 1999
Appl. No.: 09/074,739
Filed: May 8, 1998

U.S. Applications:
(60) Provisional application No. 60/046,112, filed on May 9, 1997.

(51) Int. Cl.[7] ..... A61B 17/32
(52) U.S. Cl. ..... 606/170; 606/180; 285/381.5; 285/908; 403/273; 403/270; 464/88; 464/181; 464/903; 156/293; 156/85; 156/309.6; 604/22
(58) Field of Search ..... 606/170, 171, 606/180, 159; 604/22; 464/88, 181, 903; 156/293, 85, 309.6; 285/381.5, 908; 403/273, 270

(56) References Cited

U.S. PATENT DOCUMENTS

| | | | | |
|---|---|---|---|---|
| 745,722 | A | | 12/1903 | Freeman |
| 1,630,239 | A | | 5/1927 | Binkley et al. |
| 1,636,636 | A | | 7/1927 | Humble |
| 2,878,809 | A | | 3/1959 | Treace |
| 3,379,218 | A | * | 4/1968 | Conde ..... 285/381.4 |
| 3,606,878 | A | | 9/1971 | Kellogg, Jr. |
| 3,618,611 | A | | 11/1971 | Urban |
| 3,847,154 | A | | 11/1974 | Nordin |
| 4,020,847 | A | | 5/1977 | Clark, III |
| 4,071,029 | A | | 1/1978 | Richmond et al. |

(List continued on next page.)

FOREIGN PATENT DOCUMENTS

| | | |
|---|---|---|
| AU | 215500 | 1/1957 |
| DE | 3828478 A1 | 5/1989 |
| EP | 0 393 834 | 10/1990 |
| GB | 1235321 | 6/1971 |
| JP | 61-265133 | 11/1986 |

OTHER PUBLICATIONS

American V. Mueller, "The Surgical Armamentarium", (1980) pp. 723–724.*
"Linvatec Flexes Ability With ENT Shavers", article by Troy Cozad, 1 page, published 1994 or prior thereto.

*Primary Examiner*—Michael H. Thaler

(57) ABSTRACT

The present invention is generally characterized in an angled rotary tissue cutting instrument including an outer blade assembly, having a rigid tubular member with proximal and distal portions connected by a bead, and an inner blade assembly rotatably disposed within the outer blade assembly and including a tubular drive shaft at a proximal end, a cutting tip at a distal end, and a flexible coupling disposed between the drive shaft and the cutting tip. The drive shaft and cutting tip include neck portions which are disposed telescopically within proximal and distal ends of the coupling. The flexible coupling is formed of a flexible polymeric material, and each of the neck portions includes a lateral opening defining a predetermined flow path for the polymeric material during fabrication so that the flexible polymeric coupling includes flow portions extending into the openings in the neck portions of the drive shaft and the cutting tip to form permanent, interlocking mechanical joints therewith capable of receiving and transmitting torque.

34 Claims, 7 Drawing Sheets

U.S. PATENT DOCUMENTS

| | | | |
|---|---|---|---|
| 4,239,045 | A | 12/1980 | Schlein |
| 4,265,231 | A | 5/1981 | Scheller, Jr. et al. |
| 4,445,509 | A | 5/1984 | Auth |
| 4,466,429 | A | 8/1984 | Loscher et al. |
| 4,541,423 | A | 9/1985 | Barber |
| 4,576,772 | A | 3/1986 | Carpenter |
| 4,589,412 | A | 5/1986 | Kensey |
| 4,631,052 | A | 12/1986 | Kensey |
| 4,646,738 | A | 3/1987 | Trott |
| 4,681,106 | A | 7/1987 | Kensey et al. |
| 4,690,140 | A | 9/1987 | Mecca |
| 4,696,667 | A | 9/1987 | Masch |
| 4,706,659 | A | 11/1987 | Matthews et al. |
| 4,758,204 | A | 7/1988 | Lindgren |
| 4,858,897 | A | 8/1989 | Irifune |
| 4,867,155 | A | 9/1989 | Isaacson |
| 4,998,527 | A | 3/1991 | Meyer |
| 5,152,744 | A | 10/1992 | Krause et al. |
| 5,269,785 | A | 12/1993 | Bonutti |
| 5,282,821 | A | 2/1994 | Donahue |
| 5,285,795 | A | 2/1994 | Ryan et al. |
| 5,286,253 | A | 2/1994 | Fucci |
| 5,320,635 | A | 6/1994 | Smith |
| 5,322,505 | A | 6/1994 | Krause et al. |
| 5,403,317 | A | 4/1995 | Bonutti |
| 5,411,514 | A | 5/1995 | Fucci et al. |
| 5,437,630 | A | 8/1995 | Daniel et al. |
| 5,454,827 | A | 10/1995 | Aust et al. |
| 5,510,070 | A | 4/1996 | Krause et al. |
| 5,514,151 | A | 5/1996 | Fogarty et al. |
| 5,529,580 | A | 6/1996 | Kusunoki et al. |
| 5,540,706 | A | 7/1996 | Aust et al. |
| 5,540,708 | A | 7/1996 | Lim et al. |
| 5,577,517 | A | 11/1996 | Bonutti |
| 5,593,416 | A | 1/1997 | Donahue |
| 5,601,586 | A | 2/1997 | Fucci et al. |
| 5,618,294 | A | 4/1997 | Aust et al. |
| 5,620,415 | A | 4/1997 | Lucey et al. |
| 5,620,447 | A | 4/1997 | Smith et al. |
| 5,690,660 | A | 11/1997 | Kauker et al. |
| 5,694,951 | A | 12/1997 | Bonutti |
| 5,707,350 | A | 1/1998 | Krause et al. |
| 5,741,286 | A | 4/1998 | Recuset |
| 5,839,847 | A | 11/1998 | Patel |
| 5,851,212 | A | 12/1998 | Zirps et al. |

* cited by examiner

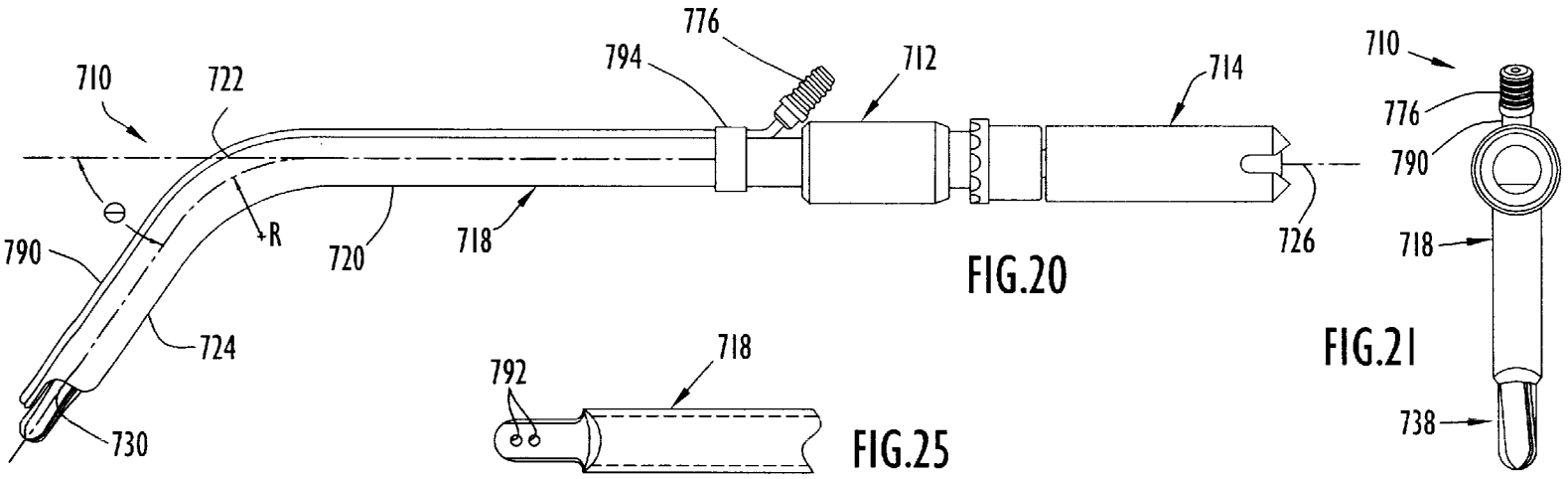
FIG.21
FIG.20
FIG.25
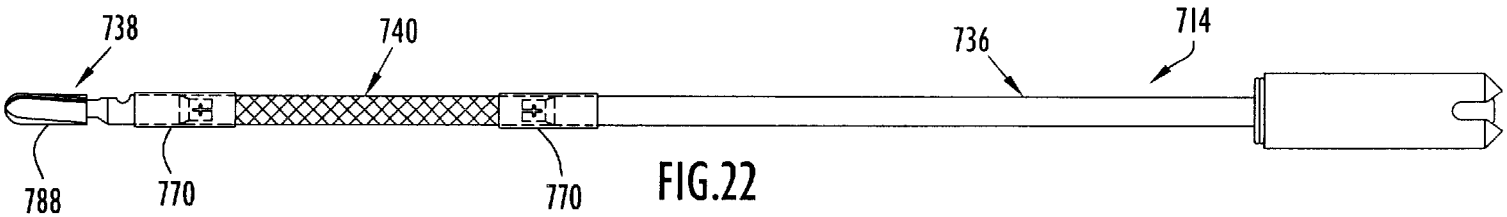
FIG.22
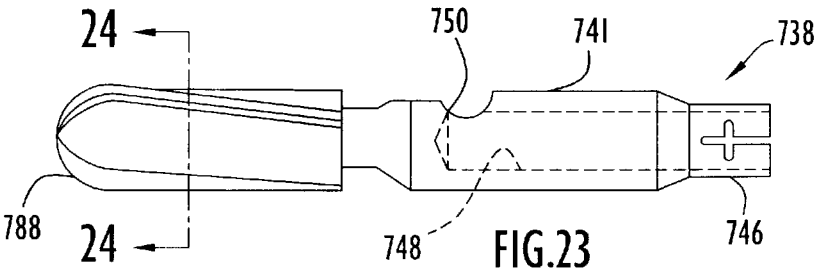
FIG.23
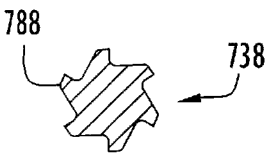
FIG.24

ANGLED ROTARY TISSUE CUTTING INSTRUMENT AND METHOD OF FABRICATING THE SAME

Matter enclosed in heavy brackets [ ] appears in the original patent but forms no part of this reissue specification; matter printed in italics indicates the additions made by reissue.

CROSS-REFERENCE TO RELATED APPLICATIONS

This application claims the benefit of U.S. Provisional Patent Application Ser. No. 60/046,112, filed May 9, 1997, the disclosure of which is incorporated herein by reference.

BACKGROUND OF THE INVENTION

1. Field of the Invention

The present invention relates generally to surgical cutting instruments and, more particularly, to surgical cutting instruments having an elongate inner member rotatably disposed within an elongate outer tubular member having a cutting window at a distal end which cooperates with or permits the inner member to cut or abrade bodily tissue.

2. Discussion of the Related Art

Surgical cutting instruments in which an elongate inner member is rotated within an elongate outer tubular member have become well accepted in surgical procedures where access to the surgical site is gained via a narrow portal or passage. Typically, the outer tubular member includes a distal end with an opening for defining a cutting port or window and the inner member includes a distal end with a cutting tip for engaging bodily tissue via the opening. Proximal ends of the inner and outer members are commonly secured to hubs which attach to a handpiece having a motor for rotating the inner member relative to the outer tubular member. The distal end of the inner member can have various configurations dependent upon the surgical procedure to be performed, with the opening in the distal end of the outer tubular member being suitably configured to cooperate with the particular configuration of the distal end of the inner member to cut, resect or abrade tissue. Often the inner member is tubular so that the loose tissue resulting from a cutting, resecting or abrading procedure can be aspirated through the hollow lumen of the inner member.

While most of the aforementioned surgical cutting instruments have a straight, elongate outer tubular member and a straight, elongate inner tubular member concentrically disposed in the outer tubular member, angled configurations have been produced in which respective axes of the distal tips of the inner and outer tubular members are offset or bent at a fixed angle relative to respective axes of the proximal ends of the inner and outer members. Examples of such fixed-angle, rotary tissue cutting instruments are shown in U.S. Pat. No. 4,646,738 to Trott and U.S. Pat. No. 5,152,744 to Kraus et al. Variable-angle rotary tissue cutting instruments, such as that described in U.S. Pat. Nos. 5,411,514 and 5,601,586 to Fucci et al, permit the user to bend the outer tube to a user-selected angle while still enabling the inner tube to be selectively inserted into and removed from the outer tube; however, known fixed-angle and variable-angle rotary tissue cutting instruments typically have a bend with a radius of curvature on the order of about 2 to 4 inches and are typically not capable of being bent beyond 15°. While the relatively small bend angle and relatively large radius of curvature of these angled tissue cutting instruments is generally suitable for most types of arthroscopic surgery, such instruments are of little use in certain types of head and neck surgery because they are not able to access surgical sites such as the maxillary sinus area which is normally accessed with hand instruments such as ball elevators and suction probes having bend angles of about 40° and radii of curvature of the order of 1.5 inches or less. Accordingly, it would be desirable for a rotary tissue cutting instrument to operate over an increased range of bend angles while at the same time reducing the radius of curvature of the bend for use in head and neck surgery.

In straight rotary tissue cutting instruments, the elongate tubular body or shaft of the inner member is generally integrally formed with the cutting tip and the proximal end of the shaft is generally permanently affixed to a plastic hub. In the case of fixed-angle rotary tissue cutting instruments, however, a flexible coupling is generally interposed between the tubular drive shaft and the cutting tip. In U.S. Pat. No. 5,620,415 to Lucy et al, U.S. Pat. No. 5,620,447 to Smith et al and U.S. Pat. No. 5,152,744 to Kraus et al, the flexible coupling is merely a portion of the inner member which is provided with relief apertures formed in the cylindrical surface to enable the inner member to bend as it rotates. In U.S. Pat. No. 5,529,580 to Kusunoki et al, U.S. Pat. No. 4,646,738 to Trott, U.S. Pat. No. 5,437,630 to Daniel et al, and U.S. Pat. Nos. 5,286,253, 5,411,514 and 5,601,506 to Fucci et al, the flexible coupling is formed of a plurality of counter-wound coiled metallic springs bonded to and interposed between the tubular body and the cutting tip.

One disadvantage of known flexible couplings is their inability to transmit sufficient torque at high speeds through angles much greater than 15° and bend radii less than 2.0 inches. In the case of flexible couplings in the form of coiled springs, there is also the possibility that gaps will develop between the coils as the coupling bends thereby resulting in a decrease of vacuum through the lumen of the inner member and a diminution of the ability of the instrument to aspirate loose tissue through the lumen. Another disadvantage associated with the use of a coiled springs as flexible couplings is the tendency of such members to require tightening or preloading when torque is applied before they are capable of transmitting the torque to the cutting tip. Also, coiled metallic springs have a tendency under certain loading conditions to relax or unwind, and thus expand, thereby increasing the possibility of the inner member binding within the outer member.

SUMMARY OF THE INVENTION

Accordingly, it is a primary object of the subject invention to overcome the abovementioned disadvantages of the prior art and to improve angled rotary tissue cutting instruments by providing a rotary tissue cutting instrument capable of operating over an increased range of bend angles while at the same time reducing the radius of curvature of the bend for use in head and neck surgery and other parts of the body.

The present invention is generally characterized in an angled rotary tissue cutting instrument including an outer blade assembly, having a rigid tubular member with proximal and distal portions connected by a bend, and an inner blade assembly rotatably disposed within the outer blade assembly and having a tubular drive shaft at a proximal end, a cutting tip at a distal end, and a flexible coupling disposed between the drive shaft and the cutting tip. The drive shaft and cutting tip include neck portions which are disposed telescopically within proximal and distal ends of the coupling. The flexible coupling includes a tubular member formed of a flexible polymeric material, and each of the neck portions includes a lateral opening defining a predetermined flow path for the polymeric material during fabrication so that the flexible polymeric coupling includes inwardly extending portions molded in the place within the openings in the neck portions of the drive shaft and the cutting tip to form permanent, interlocking mechanical joints therewith capable of receiving and transmitting torque. In one embodiment, a pair of bands formed of shrink wrap tubing are disposed around the flexible polymeric coupling adjacent respective proximal and distal ends of the coupling to provide compression directing the flow of polymeric material into the openings in the neck portions during fabrication and to provide a pair of lubricious bearing surfaces at opposite ends of the bend during operation. The flexible coupling can also include a plurality of wires embedded within the polymeric tubular member as reinforcement, the wires preferably being arranged in a plurality of layers wound in opposite directions of angles of about 45° relative to the longitudinal axis of the coupling to define a mesh-like structure within the polymeric coupling capable of transmitting torsional forces regardless of the direction of rotation while at the same time being unable to support compressive forces. Using a polymeric coupling in the above manner permits the distal portion of the outer blade assembly to be oriented at angles greater than 30° relative to the longitudinal axis of the proximal portion and the distal direction with bend radii equal to or less than 1.5 inches.

Another aspect of the present invention is generally characterized in a method of fabricating an angled rotary tissue cutting instrument including the steps of positioning a neck portion at the proximal end of a cutting tip in the distal end of a flexible polymeric coupling of tubular configuration, positioning a neck portion at the distal end of a drive shaft in the proximal end of the flexible polymeric coupling, placing a first band of shrink tubing over a proximal end of the flexible polymeric coupling, placing a second band of shrink tubing over a distal end of the flexible polymeric coupling, heating the shrink tubing and the flexible polymeric coupling to cause the polymeric coupling to flow and the shrink tubing to contract around the polymeric coupling such that the polymeric material flows along predetermined flow paths defined by lateral openings in the neck portions of the drive shaft and cutting tip, and cooling the shrink tubing and the flexible polymeric coupling so that flowed portions of the polymeric coupling harden within the openings in the neck portions to form permanent, interlocking mechanical joints therewith capable of receiving and transmitting torque as an integral blade assembly.

Some of the advantages of the present invention over the prior art are that permanent, interlocking joints can be formed between a flexible coupling and other rotating components of an inner blade member in a rotary cutting instrument without the use of adhesives or pins, that a wider range of manufacturing tolerances and clearances can be accommodated when forming such joints, that torsional forces can be more efficiently transmitted while allowing the coupling to bend, that preloading of the coupling is not required to transmit torsional forces, and that fluid leakage through the inner blade member is minimized.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 20 is a side view, in elevation, of another modification of the angled rotary cutting instrument according to the present invention.

FIG. 21 is a rear view, in elevation, of the angled rotary cutting instrument shown in FIG. 20.

FIG. 22 is a side view, in elevatiin, of an inner blade member for use with the modified angled rotary cutting instrument shown in FIG. 20.

FIG. 23 is an enlarged side view, in elevation, of a cutting tip for use with the modified angled rotary cutting instrument shown in FIG. 20.

FIG. 24 is a sectional front view of the cutting tip taken through line 24—24 in FIG. 22.

FIG. 25 is a bottom plan view of an outer blade member for use with the modified angled rotary tissue cutting instrument as shown in FIG. 20.

DETAILED DESCRIPTION OF THE PREFERRED EMBODIMENTS

Figures 1, 2, 3, 11, 12:
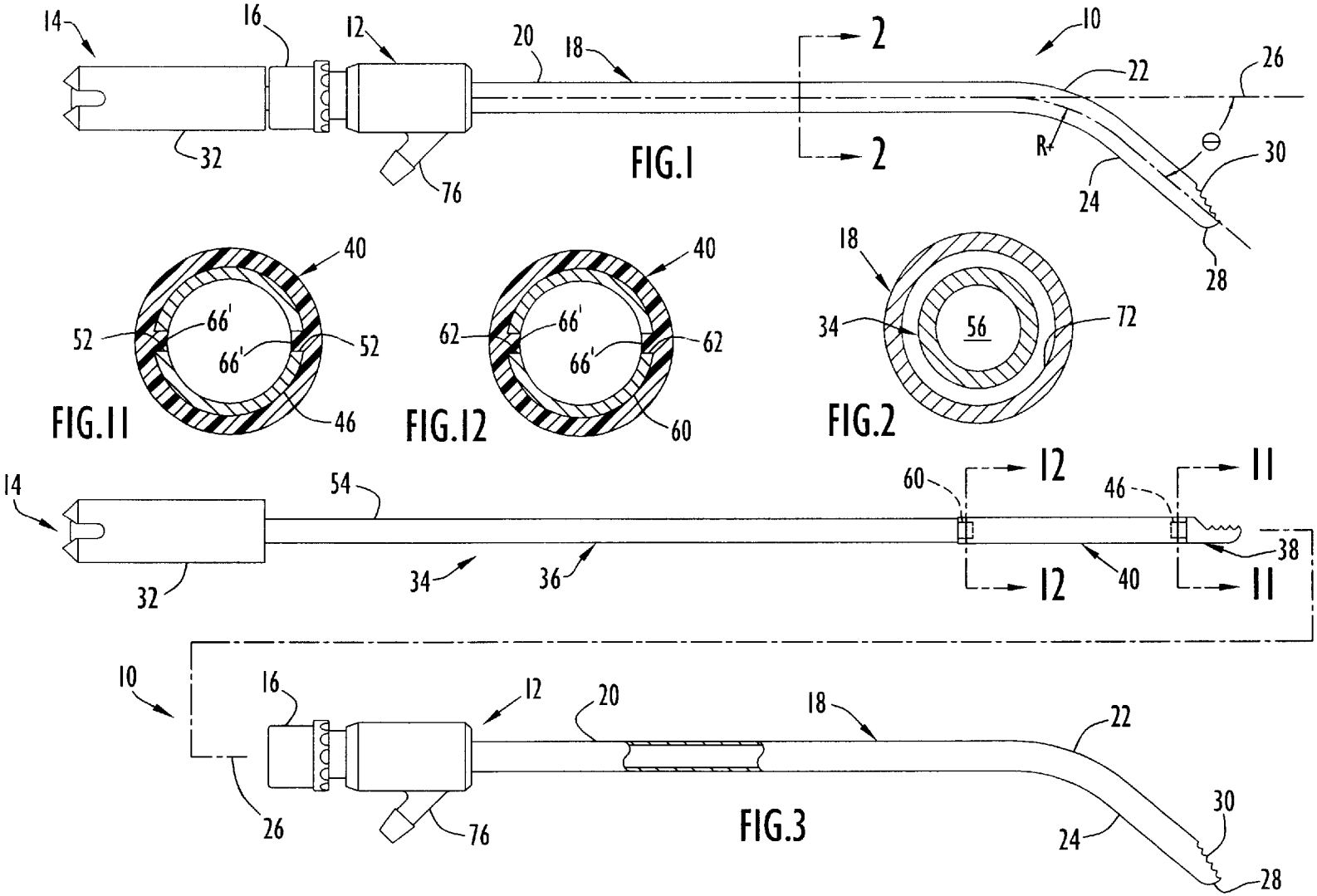
FIG. 1 is a side view of a rotary tissue cutting instrument according to the present invention.
FIG. 2 is a cross-sectional view of the rotary tissue cutting instrument according to the present invention taken through line 2—2 in FIG. 1.
FIG. 3 is an exploded side view, partly in section, of the rotary tissue cutting instrument shown in FIG. 1.
FIG. 11 is a cross-sectional view of the inner tubular member taken along line 11—11 in FIG. 3.
FIG. 12 is a cross-sectional view of the inner tubular member taken along line 12—12 in FIG. 3.

A rotary tissue cutting instrument or blade 10 according to the present invention, as illustrated in FIGS. 1–3, includes an outer blade member or assembly 12 and an inner blade member or assembly 14 rotatably received within the outer blade member. Outer blade member 12 includes a hub 16 and an outer tubular member or sleeve 18 having a proximal portion 20 of straight configuration extending distally from the hub to a bend 22 connecting the proximal portion with a distal portion 24 oriented at an angle θ of about 40° relative to the longitudinal axis 26 of the proximal portion. Angled portion 24 of the outer tubular member extends downwardly from bend 22, looking at FIG. 1, to a rounded distal end 28 having an opening facing upwardly, away from the center of curvature of the bend, to define a cutting port or window 30. The orientation of the cutting window as well as the radius of curvature and location of the bend relative to the distal end of the angled portion are dependent upon the procedure to be performed. For example, in FIG. 1, the bend is shown with a radius of curvature R of about 0.875 inches and is located about 0.7 inches from the distal end of the angled portion with the window facing outwardly, relative to the center or curvature, to facilitate use of the instrument as an adenoid blade.

Inner blade member 14 includes a hub 32 disposed proximally of the outer member hub and an elongate tubular portion 34 extending distally from the hub to be disposed coaxially within the outer tubular member. The elongate tubular portion of inner member 14 includes a relatively rigid, tubular drive shaft 36 at a proximal end, a cutting tip 38 at a distal end, and a flexible coupling 40 disposed between the drive shaft and the cutting tip adjacent the bend in the outer tubular member to transmit torque from a motorized handpiece (not shown) to the cutting tip while allowing the tubular portion of the inner member to conform to the angled shape of the outer tubular member.

Figure 4:
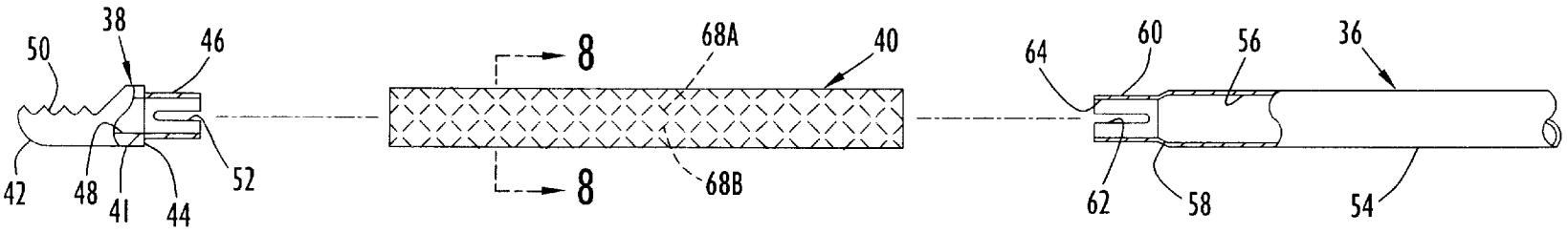
FIG. 4 is an exploded side view, partly in section, of an inner tubular member for use with the rotary tissue cutting instrument according to the present invention.
Figure 5:
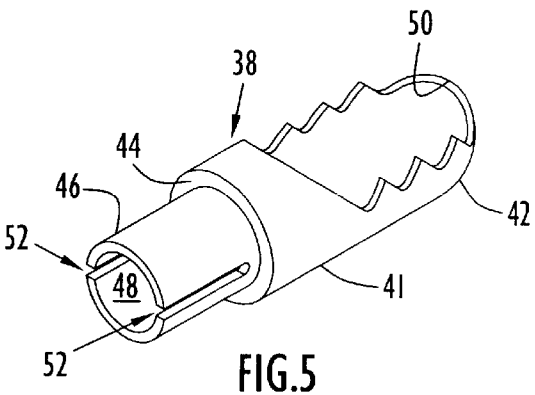
FIG. 5 is a perspective view of a cutting tip for the inner tubular member shown in FIG. 4.
Figure 6:
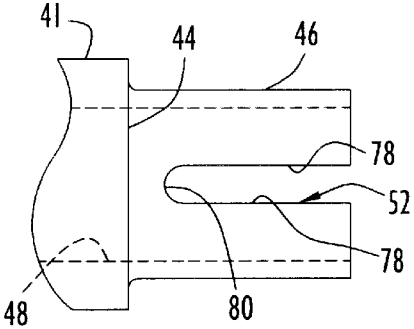
FIG. 6 is a fragmentary side view of a neck configuration for the cutting tip and tubular drive shaft.

As best seen in FIGS. 4–6, cutting tip 38 includes a hollow, cylindrical body 41 extending from a generally rounded distal end 42 to a radial step or shoulder 44 where the diameter of the cutting tip decreases to define a hollow, tubular neck 46 of smaller diameter than the cylindrical body. A passage or lumen 48 is formed longitudinally through the cutting tip, and an opening 50 is formed through side and end walls of the distal end of the cutting tip in communication with the lumen to form a section inlet through which loose tissue can be aspirated. Peripheral edges of opening 50 form a cutting edge at the distal end of the cutting tip, the distal end of the cutting tip being disposed adjacent the window at the distal end of the outer tubular member to permit the cutting edge to engage bodily tissue via the window. Neck 46 is of generally cylindrical configuration and, as best seen in FIG. 6, a pair of openings in the form of elongate, longitudinal slots 52 are formed through the neck in diametrically opposed relation, each of the slots including a pair of parallel edges 78 extending distally from a proximal edge of the neck and terminating at a full radius 80. As will be described in greater detail below, the slots are used to define a predetermined flow path for the polymeric material of the flexible coupling during fabrication so that a portion of the polymeric material will extend through the wall thickness of the neck and conform substantially to the shape of the slots to form a permanent joint for directly receiving and transmitting torque without relying on shear forces applied via friction or through an adhesive layer.

Figure 7:
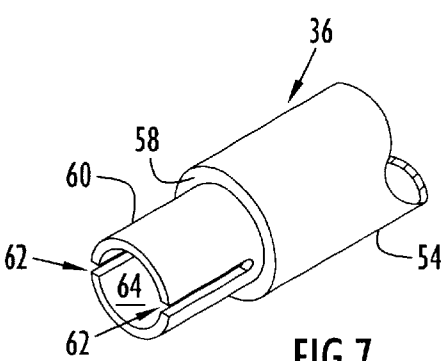
FIG. 7 is a perspective view of the distal end of a tubular drive shaft for the inner tubular member of FIG. 4.

Referring to FIGS. 4 and 7, drive shaft 36 includes an elongate, cylindrical body 54 of hollow configuration defining a lumen 56 somewhat larger than the cutting tip lumen, the elongate cylindrical body of the drive shaft extending distally from hub 32 to a radial step or shoulder 58 where the drive shaft decreases in diameter to define a hollow, tubular neck 60 with slots 62 substantially similar to tubular neck 46, the drive shaft neck defining a lumen 64 similar in size to the lumen defined through the cutting tip so that tissue aspirated via the cutting tip lumen will not clog the drive shaft.

Figure 8:
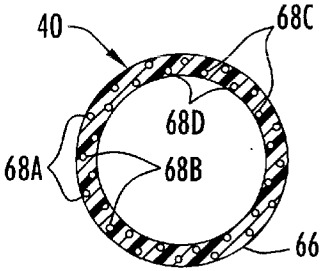
FIG. 8 is a cross-sectional view of a flexible coupling for use with the inner tubular member taken along line 8—8 in FIG. 4.

Flexible coupling 40 includes a hollow tubular member formed of a reinforced polymeric material. In a presently preferred embodiment, the polymeric matrix material 66 is a flexible polyurethane, such as NEUTHANE, having a hardness of about 72 durometer, Shore A, and the reinforcement or stiffening members are a plurality of fine gage stainless steel wires embedded within the polymeric matrix material as shown by broken lines at 68A and 68B in FIG. 4. The wires are arranged in layers, each layer being made up of a plurality of circumferentially spaced, helically intertwined wires wound at angles of about 45' relative to the longitudinal axis of the tubular coupling member. Unlike springs, which are formed of a single length of relatively heavy gage spring wire wound tightly into a coil, the wires used to reinforce the polymeric tubular member are of a fine gage (e.g., 0.002×0.004 inches in cross-section) and are only loosely wound (e.g., at 45° angles) so that while the reinforcement wires tend to be strong in tension they are generally unable to support compressive forces. For this reason, the wires in adjacent layers are counterwound (i.e., wound in opposite directions) such that adjacent layers of wires cross one another substantially orthogonally to define a woven or mesh-like reinforcing structure which guarantees that at least one layer of wires will be placed in tension as a result of a torsional force to stiffen the flexible coupling irrespective of the direction of rotation while offering little or no resistance to bending. At the same time, the inability of the wires to support compressive forces means that the wires will not deform the flexible coupling in response to compressive forces caused by counter rotation. In a presently preferred embodiment, shown in FIG. 8, two layers of wires 68A and 68B are embedded near the outer surface of the polymeric tubular member and two layers of wires 68C and 68D are embedded near the inner surface of the polymeric tubular member to give greater stiffness. Each layer preferably includes eight wires; however, fewer than eight wires or more than eight wires can be used dependent upon the stiffness required.

Figure 9:
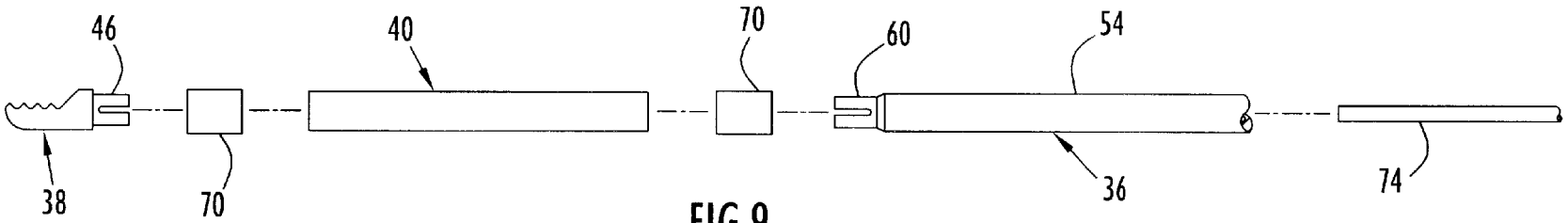
FIGS. 9 and 10 are side views illustrating fabrication of the inner tubular member according to the present invention.
Figure 10:
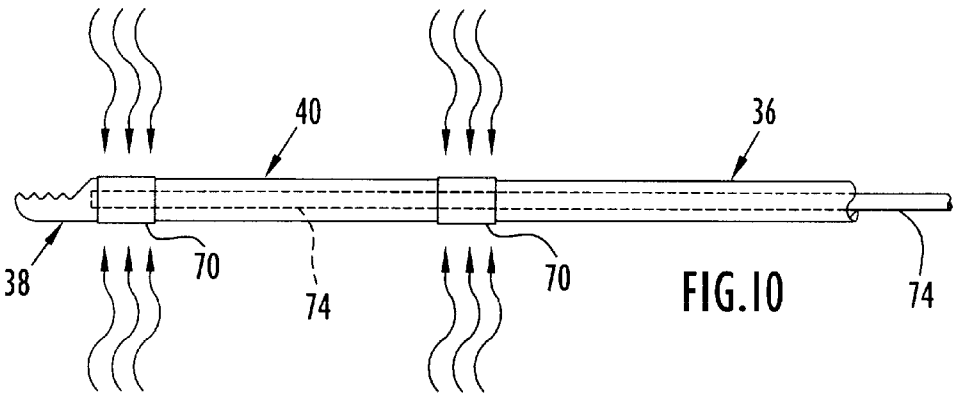

A method of securing the flexible coupling 40 between the cutting tip 38 and the tubular drive shaft 36 in accordance with the present invention, as illustrated in FIG. 9 and 10, involves inserting the neck 46 at the proximal end of the cutting tip into the open distal end of the flexible coupling, inserting the neck 60 at the distal end of the drive shaft into the open proximal end of the flexible coupling, and positioning a pair of bands or collars 70 formed of heat shrink tubing, for example TEFLON tubing, at opposite ends of the flexible coupling around the neck portions of the cutting tip and the drive shaft. The assembly is then heated, preferably using an induction heating process, to cause the polymeric material 66 of the flexible coupling to flow and the bands or collars to shrink, thereby forcing the polymeric material to flow radially inward into the slots 52 and 62 formed in the necks while maintaining a smooth outer surface for the flexible coupling and preventing the reinforcement wires from buckling or otherwise becoming displaced at opposite axial ends of the flexible coupling. The flowing polymeric material is received within the slots, which define a predetermined flow path for the polymeric material of the flexible coupling, such that a portion 66' of the polymeric material will extend through the wall thickness of the neck and conform substantially to the shape of the slots to form a permanent, interlocking mechanical joint, as shown in FIGS. 11 and 12, for directly receiving and transmitting torque without adhesives or pins. By providing a space into which the polymeric material can flow, slots 52 and 62 also prevent the polymeric material from bulging out the sides of the shrink wrap tubing and obstructing the irrigating channel 72 or causing the inner blade member to bind. Preferably, a cylindrical mandrel 74 is inserted telescopically through the lumen of the inner blade member prior to the heating step to maintain a smooth, non-occluding interior surface for the lumen by preventing or controlling leakage of the polymeric material from the slots into the lumen. A suitable mandrel for this purpose has been made out of tool steel but can be made out of any suitable material. Typically, the mandrel and heat shrink tubing are removed after the polymeric material has cured; however, the heat shrink tubing can be left in place to form one or more lubricious bearing surfaces if desired.

The rotary tissue cutting instrument is assembled for use by inserting the cutting tip 38 of the inner blade member 14 into the proximal end of hub 16 of the outer blade member and attaching the hubs 16 and 32 to a conventional motorized handpiece (not shown), such as the Wizard™ or Straightshot™ handpieces manufactured by Xomed Surgical Products of Jacksonville, Fla., such that the outer member 12 is held substantially stationary relative to the handpiece while permitting the inner member 14 to rotate within the outer member. At this point, tubular portion 34 of the inner blade member is disposed concentrically within the outer blade member with cutting tip 38 of the inner blade member being disposed adjacent cutting window 30 at the distal end of the outer blade member and flexible coupling 40 disposed within bend region 22 of the outer blade member. When the handpiece motor is actuated, the outer blade member 12 remains substantially stationary relative to the handpiece while the inner blade member 14 is rotated. More specifically, actuation of the handpiece motor causes hub 32 at the proximal end of the inner blade member to rotate. Tubular drive shaft 36 of the inner blade member is rigidly attached to hub 32 and is thus rotated in the same direction as the hub, along with neck 60 at the distal end of the tubular drive shaft. Portion 66' of flexible coupling 40 which are molded or embedded within slots 52 in the neck are caused to rotate with the tubular drive shaft, thereby applying torsional forces at the proximal end of the flexible coupling. The torsional forces applied at the proximal end of the coupling are generally resolved into shear forces which act an angle of about 45° relative to the longitudinal axis of the coupling and thus load half the wires 68A or B and 68C or D in each wire layer of the coupling substantially in tension. Since the wires offer greater stiffness in tension, the torsional forces applied at the proximal end of the flexible coupling are efficiently transmitted to the distal end of the coupling for transmission to the cutting tip via coupling portions 66' embedded or molded within slots 62 in the neck 46 of the cutting tip 38. The wires are immediately placed in tension due to their orientation in alignment with the shear forces generated by the torsional forces and the fact that the wires are not configured like springs which must generally be preloaded before being able to transfer torsional loads; however, since the wires are loosely coiled, the flexible coupling is easily bent. Accordingly, the flexible coupling will effectively transmit torque from the drive shaft to the cutting tip even at high speeds (e.g., between about 300 r.p.m. and about 6000 r.p.m.) and when the coupling is bent at angles greater than 30° relative to the distal direction. If a polyurethane such as NEUTHANE is utilized in forming the flexible coupling, the high lubricity of the material will also minimize thermal effects, gouging and galling which can be caused by frictional contact between the inner and outer members.

Outer member hub 16 is shown with an optional nipple 76 extending proximally from a side of the hub at an acute angle relative to the longitudinal axis of the straight portion of the outer tubular member. The nipple communicates with the annular space or channel 72 between the inner and outer tubular members so that, when a source of fluid is connected with the nipple, fluid will be supplied to the operative site via the annular channel, for example to irrigate the site or clear blockages. Irrigating fluids can also be provided at the operative site via tubes disposed externally of the outer tubular member as disclosed, for example, in application Ser. No. 08/497,117, the disclosure of which is incorporated herein by reference. Suction or aspiration may be provided at the operative site via the lumen 48, 56 and 64 extending through the inner blade member.

The reduced diameter necks at respective proximal and distal ends of the cutting tip and the drive tube, respectively, can have any configuration to be snugly received within the flexible coupling. In the embodiment described above, however, the neck is about 0.02 inches smaller in diameter than the body of the cutting tip or the drive shaft and the slots are approximately 0.120 inches long and about 0.020 inches wide.

Figure 13:
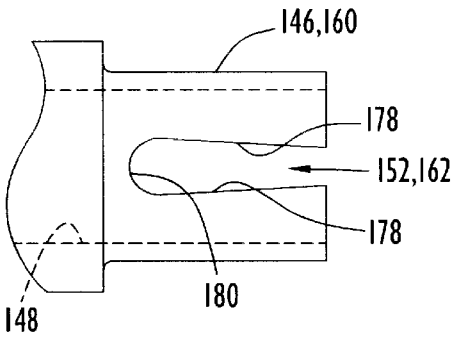
FIGS. 13–16 are fragmentary side views illustrating modifications of the neck configuration for the cutting tip and tubular drive shaft.
Figure 16:
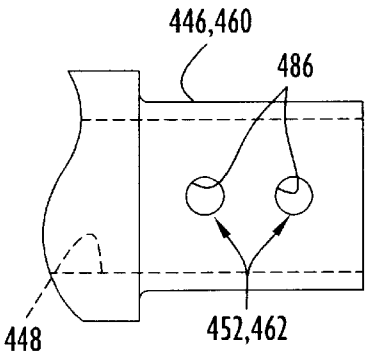
Figure 15:
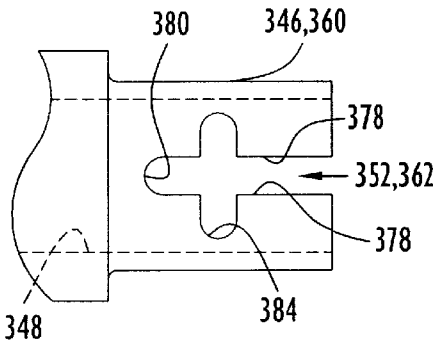
Figure 14:
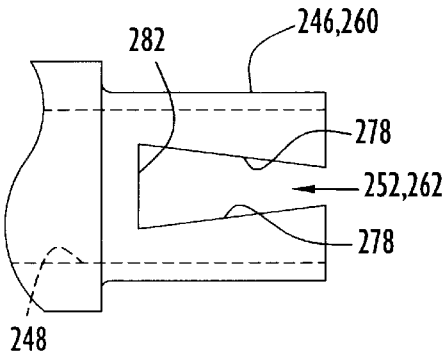

The slots 52 and 62 shown and described above for defining predetermined flow paths in relation to respective neck portions of the cutting tip and drive shaft are merely exemplary of the types of openings that can be formed in or through a neck for this purpose. For example, in FIG. 13, a modification of a neck portion 146,160 suitable for use at the proximal end of the cutting tip or the distal end of the drive shaft includes an opening 152, 162 in the form of a slot having laterally opposed edges 178 angled away from one another in the direction of a full radius 180 at the terminal end of the slot to improve resistance of the joint to longitudinal separation. In FIG. 14, another modification of a neck portion is shown at 246,260 wherein the opening 252, 262 is in the form of a slot having a truncated triangular configuration with laterally opposed edges 278 angled away from one another in the direction of a straight edge 282 transversely connecting terminal ends of the angled edges to improve resistance of the joint to longitudinal separation. Yet another modification of a neck portion is shown in FIG. 15 at 346,360 wherein the neck includes an opening 352, 362 in the form of a cruciform having a first longitudinal slot similar to slot 52, 62 and a second slot 384 oriented transverse to the first slot to improve resistance of the joint to longitudinal separation. The modification of a neck portion shown in FIG. 16 at 446, 460 includes openings 452,462 in the form of a pair of longitudinally spaced and laterally aligned through-holes 486 which do not communicate with the peripheral edge of the neck like the other openings. The openings could also include recesses, knurling and slots oriented at angles relative to a longitudinal axis of the neck. It will also be appreciated that one slot or opening or more than two slots or openings can be formed through a neck in accordance with the present invention.

The overall length of the rotary cutting instrument 10 as well as the location of the bend, the bend angle, radius of curvature and other dimensions are dependent upon the type of surgery to be performed. In a presently preferred embodiment, particularly suitable for adenoid surgery, the rotary cutting instrument 10 has an overall length of about 6.0 inches when assembled, with bend 22 having a radius of curvature of about 0.875 inches and a bend location about 0.7 inches from the distal end of the outer tubular member. Cutting window 30 is disposed on a side of the outer tubular member opposite the center of curvature of the bend and is preferably formed by an angled cut with a bevel angle of about 13° relative to a longitudinal axis of the angled or distal portion. Distal portion 24 of the outer tubular member can be oriented at any angle between 35° and 60° relative to proximal portion 20 but is preferably oriented at an angle of about 40° for adenoid surgery.

Figure 17:
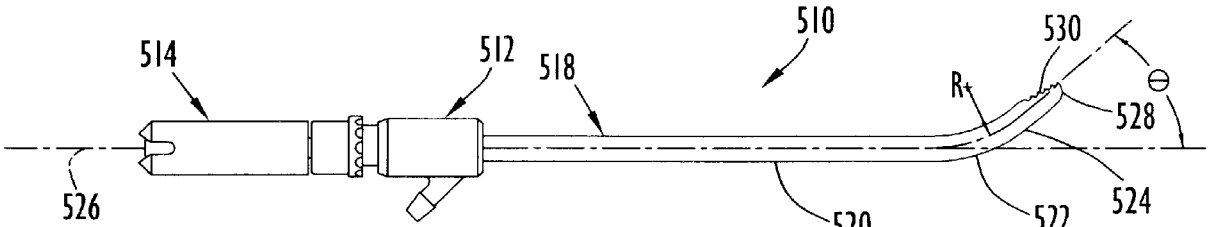
FIGS. 17 and 18 are side views illustrating further modifications of the rotary tissue cutting instrument according to the present invention.

FIG. 17 illustrates another modification of the rotary cutting instrument according to the present invention wherein the modified rotary cutting instrument 510 is similar to rotary cutting instrument 10 but is adapted to allow access into the maxillary sinus and frontal recess. Outer blade member 512 of the modified rotary cutting instrument includes an outer tubular member 518 with a relatively long proximal portion 520 of straight configuration and a bend 522 connecting the proximal portion with a relatively short distal portion 524 oriented at an angle θ relative to the longitudinal axis 526 of the proximal portion. Like rotary cutting instrument 10, the modified instrument can have any suitable dimensions but is preferably configured to have an overall length of about 6.0 inches, with the distal portion 524 being oriented at an angle of about 40° relative to the longitudinal axis 526 of proximal portion 520, and with bend 522 having a radius of curvature of about 0.875 inches; however, bend 522 is preferably located closer to the distal end of the outer tubular member, e.g. about 0.425 inches, with cutting window 530 of the modified instrument being formed on a side of the outer tubular member facing toward the center of curvature and being formed by an angled cut like the cutting window described above. The inner blade member 514 for use with the modified instrument is substantially the same as the inner blade member described above since both need to bend at a location immediately adjacent the distal end of the inner blade member. The modified rotary cutting instrument 510 is useful for superior ethmoid access, frontal recess surgery, maxillary sinus polyps, maxillary antrostomy and uncinectomy.

Figure 18:
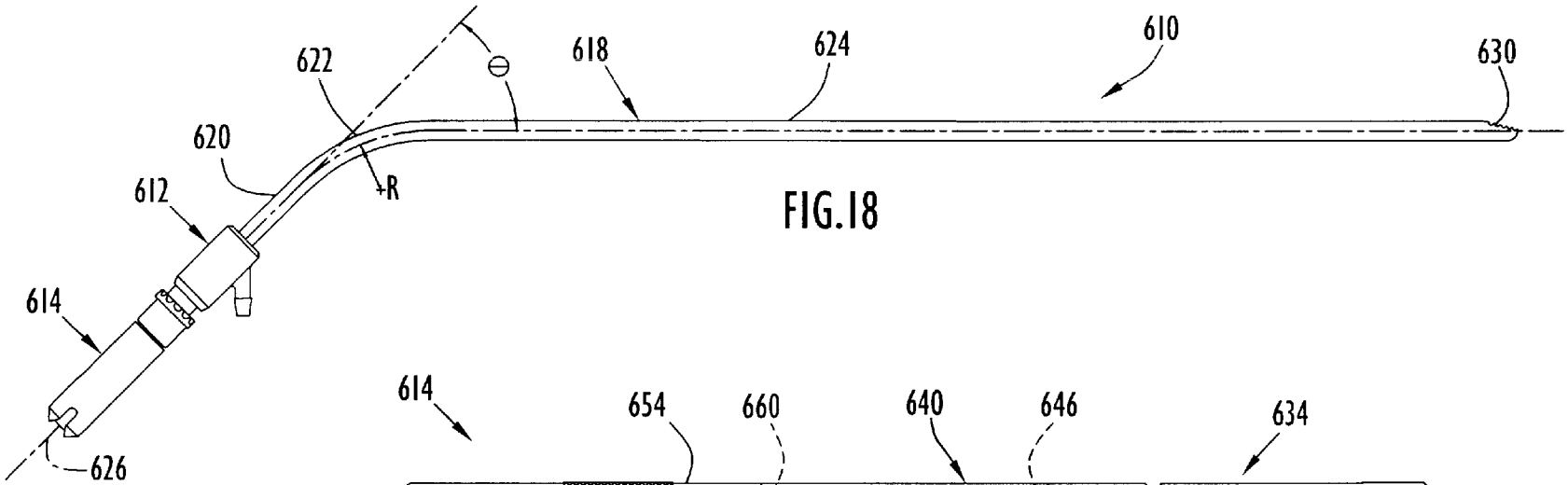
Figure 19:
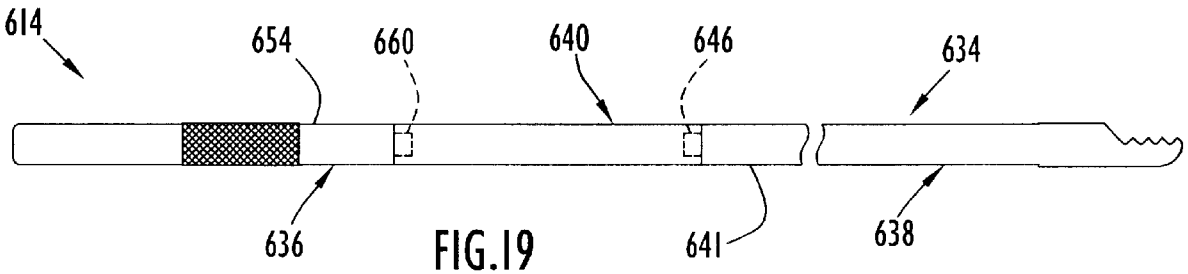
FIG. 19 is a side view, broken longitudinally, of an inner tubular member for use with the modified cutting instrument shown in FIG. 18.

Another modification of the present invention is shown in FIGS. 18 and 19 at 610 wherein the rotary cutting instrument takes the form of a laryngeal blade having an outer tubular member 618 with a relatively short proximal portion 620 of straight configuration and a relatively long distal portion 624 extending distally from a bend 622 at an angle θ relative to the longitudinal axis 626 of the proximal portion. Distal portion 624 can have any suitable length and be oriented at any angle relative to proximal portion 620. Preferably, however, distal portion 624 has a length of about 8.75 inches and is oriented at an angle of about 45° relative to the longitudinal axis 626 of proximal portion 620, with proximal portion 620 having a length of about 0.5 inch and with bend 622 having a radius of curvature R of about 1.5 inches. Cutting window 630 of the modified instrument is on a side of the outer tubular member opposite the center of curvature of the bend and is formed by an angled cut like the cutting windows described above. The inner blade member 614 is modified, however, as shown in FIG. 19 (without a hub), so that the lengths of the tubular drive shaft and cutting tip correspond to those of the proximal and distal portions of the outer tubular member, respectively, with the flexible coupling being disposed between the cutting tip and drive shaft as before but with a possibly slightly longer length to accommodate the larger bend radius.

The distal end of the cutting tip can have various configurations dependent upon the surgical procedure to be performed, with the opening in the distal end of the outer tubular member being suitably configured to cooperate with the particular configuration of the distal end of the inner tubular member. For example, the distal end of the cutting tip can have serrated or sharp edges, can include burs, drills, trephines, or brushes, and can be configured to produce side cutting, meniscus cutting, end cutting, trimming, burring or abrading, or full radius resection. In FIGS. 20–25, for example, a modification of a rotary cutting instrument according to the present invention is shown wherein the inner blade member 714 of the modified instrument 710 includes a cutting tip 738 with a bur 788. As shown in FIGS. 22 and 23, bur 788 includes a bullet-shaped body with six flutes formed therein to define cutting surfaces; however, any suitable bur configurations can be used including, but not limited to, configurations having fewer or more than six flutes and configurations where the bur is generally spherical, hemispherical, conical, pear shaped or cylindrical. Cutting tip 738 also includes a hollow, tubular neck 746 similar to the neck shown in FIG. 15 and a cylindrical portion 741, disposed between the neck and the bur, for defining a longitudinal passage or channel 748 between the neck and a lateral opening or hole 750 proximally spaced from the bur, the lateral opening defining a suction inlet through which tissue can be aspirated.

The other components of the inner blade member 714 (i.e., drive tube 736 and flexible coupling 740) are similar to those described above; however, longer lengths of shrink tubing 770 are used during the assembly process and are left in place thereafter to define a pair of spaced bearing surfaces at opposite ends of the bend 722 when the inner blade member 714 is inserted into the outer blade member 718. Since shrink tubing 770 covers only axial end portions of flexible coupling 740, the physical characteristics of the medial portion of the coupling are substantially unaffected. Specifically, the flexibility of the coupling as well as the radial spacing between the medial portion of the coupling and the outer blade member are substantially the same as described above with the added benefit of lubricious bearings surfaces immediately adjacent opposite ends of the bend.

Outer blade member 712 is similar to those described above; however, the angled distal portion 724 of the outer member 718 is shown oriented at an angle θ of about 55° relative to the longitudinal axis 726 of the straight portion 720 and the cutting window 730 is shown with relatively smooth edges in both the side and end walls of the outer member with a configuration to permit the bur 788 to protrude therefrom. The radius of curvature R of the bend can be varied but is preferably about 0.875 inch, and the bend preferably starts close to the distal end of the instrument, for example about 1.0 inch from the distal tip of the bur.

Depending on the thickness of the shrink tubing, irrigating fluids can be supplied to the operative site via the annular channel between inner and outer blade members; however, when the shrink wrap tubing is left in place, it is preferred that irrigating fluids be supplied to the operative site using a tube 790 routed along the exterior of the outer blade member as shown, for example, in FIG. 20. Tube 790 extends distally along the outer blade member from a nipple 776 to a pair of longitudinally spaced fluid supply apertures 792 formed through the wall of the outer blade member adjacent the cutting tip. In the illustrated embodiment, a distal end of tube 790 is laser welded to the distal end of the outer blade member and a proximal end of the tube is held in place by shrink tubing 794.

The rotary tissue cutting instrument according to the present invention can include a bend anywhere along the length of the outer tubular member so long as the inner tubular member is provided with a flexible coupling located in juxtaposed relation to the bend. If desired, more complex curvatures and configuration can be formed by bending the outer tubular member in more than one location and providing the inner tubular member with one or more flexible couplings in juxtaposed relation to the bends. For example, in FIGS. 26–31, a modification of a rotary tissue cutting instrument according to the present invention is shown wherein the modified instrument or blade 810 is similar to the laryngeal blade 610 shown in FIG. 18 but with two bends 822 and 822' at longitudinally spaced locations along the length of the outer tubular member 818 to improve access for certain procedures. Outer tubular member 818 includes a proximal portion 820 of straight configuration extending distally from a hub 816 to a first bend 822, an intermediate or angled portion 888 extending distally from the first bend at an angle $\theta_1$ relative to a longitudinal axis 826 of the proximal portion to a second bend 822', and a distal portion 824 extending distally from the second bend at an angle $\theta_2$ relative to a longitudinal axis 890 of the intermediate portion. For a laryngeal blade as shown, $\theta_1$ can range from about 40° to about 50° in a first direction (with 45° being preferred) and $\theta_2$ can range from 0° (FIG. 18) to about 20° in a second, opposite direction (with 15° being preferred). The bend radii $R_1$ and $R_2$ can be the same or different but, for a laryngeal blade, $R^1$ is preferably about 1.5 inches and $R_2$ is preferably about 0.875 inch, with proximal and distal portions 820 and 824 being of approximately the same length (e.g., about 0.5 inch) and the intermediate portion being considerably longer (e.g., between 8 and 10 inches) then the proximal and distal portions. Distal portion 824 defines a cutting window 830 at a distal end 828 thereof on the same side of the outer tubular member 818 as the center of curvature of second bend 822'. Distal end 828 of the outer tubular member is generally hemispherical, with cutting window 830 being formed by a bevel cut taken at an angle a (e.g., about 32°) relative to a longitudinal axis of the distal portion to produce sharp inner edges and having a radial depth D (e.g., about 0.024 inch) such that the window is a generally elliptical or round opening small enough to be located on one side of the central and longitudinal axis 892 of the distal portion.

Inner blade member 814 includes a first flexible coupling 840 disposed between the distal end of drive shaft 836 and the proximal end of a connecting tube 894, and a second flexible coupling 840' disposed between the distal end of the connecting tube and a cutting tip 838. Drive shaft 836 is similar to drive shaft 636 and includes a tubular neck 860 similar to that shown in FIG. 6. Connecting tube 894 is of hollow, cylindrical configuration as preferably formed of stainless steel having the same inner and outer diameters as drive shaft 836 (e.g., an inner diameter of about 0.102 inch and an outer diameter of about 0.122 inch). Tubular necks 896 and 898 of similar configuration to neck 860 are carried at opposite axial ends of the connecting tube to couple with flexible couplings 840 and 840', respectively. The flexible couplings are identical to those described above but are of sufficient length to extend through bends 822 and 822' in a manner allowing rotation of the inner blade member relative to the outer blade.

Figures 26, 27, 28, 29, 30, 31:
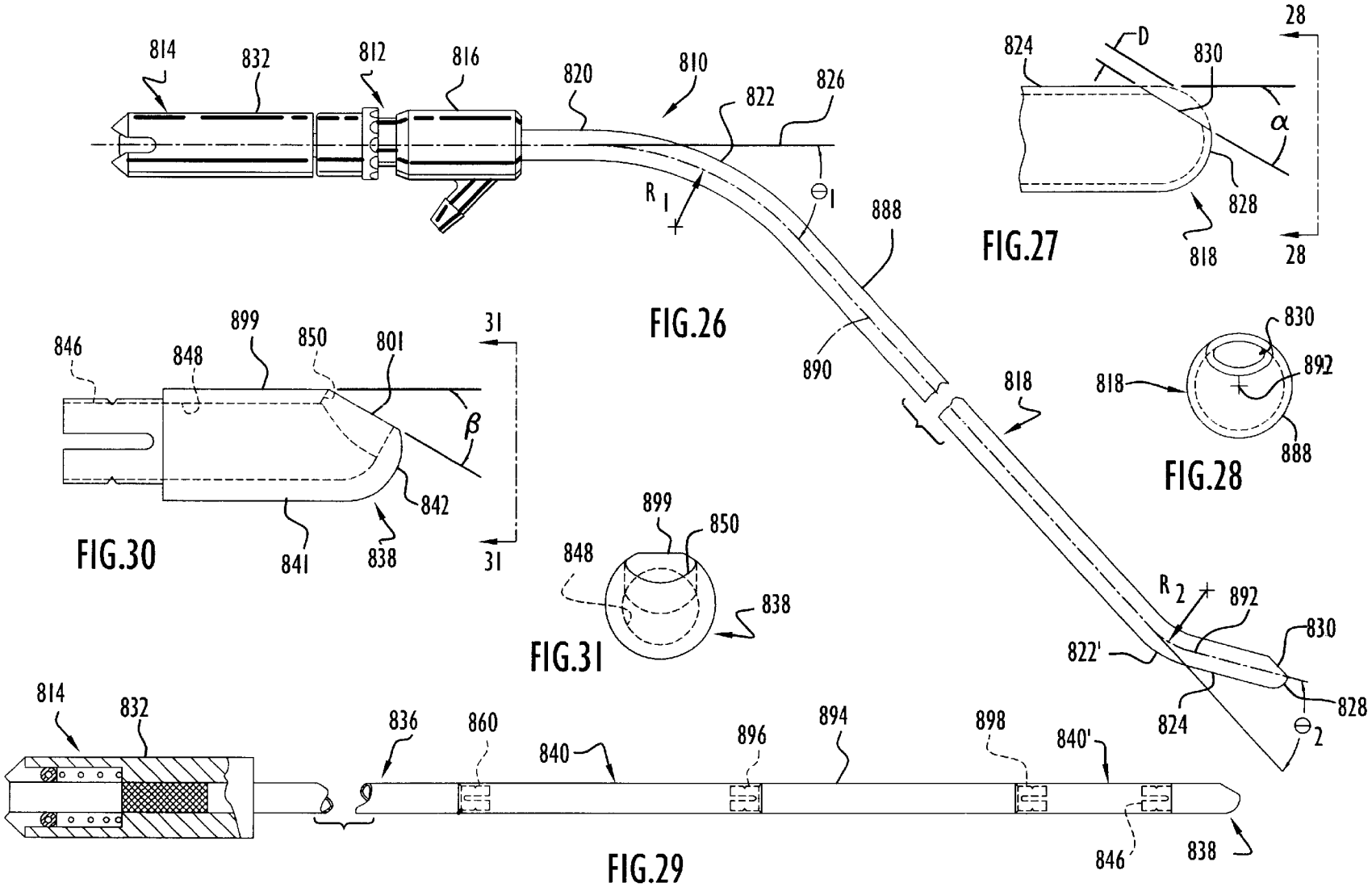
FIG. 26 is a broken side view, in elevation, of yet another modification of the angled rotary cutting instrument according to the present invention.
FIG. 27 is an enlarged fragmentary side view of the distal portion of the outer tubular member of the modified rotary cutting instrument shown in FIG. 26.
FIG. 28 is a front view of the distal portion of the outer tubular member taken through line 28—28 in FIG. 27.
FIG. 29 is a side view, in elevation, of an inner blade member for use with the modified angled rotary cutting instrument shown in FIG. 26.
FIG. 30 is an enlarged side view, in elevation, of a cutting tip for use with the modified angled rotary cutting instrument shown in FIG. 26.
FIG. 31 is a front view of the cutting tip taken through line 31—31 in FIG. 30.

Cutting tip 838 of the modified inner blade member 814 is modified to work in cooperation with cutting window 830 of the modified outer blade member 812 to cut tissue when rotated and, as best seen in FIG. 30, the cutting tip includes a generally cylindrical body 841 terminating in a generally hemispherical distal end or tip 842 configured to fit within the hemispherical tip at the distal end of the outer tubular member in a cooperative and conforming manner. A flat 899 extends longitudinally along the body of cutting tip 838 from a proximal end of the body to a beveled surface or cut 801 adjacent the distal end of the cutting tip and oriented at an angle β (e.g., about 30°) relative to the flat. A bore or opening 850 is formed into the cutting tip perpendicular to surface 801 to communicate with lumen 848 which extends longitudinally through the neck 846 at the proximal end of the cutting tip and body 841 of the cutting tip. Respective lengths of drive shaft 836, connecting tube 840, cutting tip 838, and flexible couplings 840 and 840' are chosen to position the flexible couplings in juxtaposed relation to bends 822 and 822' in the outer tubular member so that the inner blade member may rotate freely within the outer blade member to cause the cutting tip to cut tissue in cooperation with the cutting window.

From the above, it will be appreciated that the rotary tissue cutting instrument according to the present invention permits operation over an increased range of bend angles while at the same time reducing the radius of curvature of the bend for use in head and neck surgery and other parts of the body.

The cutting port or window at the distal end of the outer tubular member in the rotary tissue cutting instrument according to the present invention can be defined by a distal-facing opening, a lateral-facing opening or an opening formed in both the side wall and the end wall of the outer tubular member. In addition, the window can be oriented to face towards the center of curvature of the bend or away from the center of curvature. Peripheral edges of the window can have any configuration permitting the cutting tip to cut, shave or abrade tissue including, but not limited to configuration wherein the edges are smooth as shown in FIG. 25 or serrated as shown in FIG. 1 to define teeth.

While neck portions of the cutting tip, drive shaft and any connecting tubes are described herein as being of cylindrical configuration, it will be appreciated that the necks can have any tubular configuration in cross-section including, but not limited to, elliptical and polygonal cross-sectional configurations as well as configurations wherein the shape of the outer surface of the neck is different than the shape of the inner surface of the neck.

The flexible coupling can be located anywhere along the length of the inner blade member dependent upon the procedure to be performed. Furthermore, more than one flexible coupling can be used to accommodate more complex curvatures. Although the flexible coupling is described herein as being formed of a polyurethane reinforced with stainless steel wires, it will be appreciated that other polymeric materials can be used as the matrix material and that various metallic, ceramic and polymeric materials can be used as reinforcing members dependent upon the combination of materials and intended use. It will also be appreciated that the number of reinforcing members can be fewer or more than the number shown herein and that the reinforcing members can, for example, be of rectangular, elliptical or asymmetrical cross-section dependent upon the number and size of the reinforcing members. The flexible coupling could also be formed of a non-reinforced polymeric material provided that the material is capable of transmitting torque when bent at angles exceeding 30°. In the case of the second angle in FIG. 26, the flexible coupling need not necessarily be capable of transmitting torque when bent at angles exceeding 30°.

Proximal and distal portions of the outer tubular member are preferably formed as an integral one-piece unit from a relatively rigid, medically acceptable material such as Type 304 stainless steel, but can be formed of any suitable material and/or be formed separately and coupled together. In a preferred embodiment, the outer tubular member has an outer diameter of about 0.12 to about 0.16 inch with a wall thickness of about 0.02 inch; however, other diameters and wall thicknesses can be used. The inner and outer blade member hubs can be of conventional configuration to mate with any suitable handpiece and can be made of any relatively rigid, medically acceptable material. The cutting tip can also be formed of any suitable material but is preferably formed of a relatively rigid, medically acceptable material capable of carrying a cutting edge, such as stainless steel. The tubular drive shaft can also be formed of stainless steel or any other relatively rigid, medically acceptable material. Proximal ends of the inner and outer blade members can be provided with knurled surfaces which extend about the circumference of the members to mate frictionally with the hubs.

The rotary tissue cutting instrument can be adapted to accept accessories such as, for example, electrocautery, fiber optics, and laser fibers. Such accessories can, for example, be associated with the outer tube but follow the curved surfaces to the tip of the instrument.

When more than one bend is formed in the outer tubular member of the rotary tissue cutting instrument according to the present invention, the bends can be in the same plane as shown in FIG. 26 or in different planes dependent upon the procedure for which the instrument is designed.

The features of the various embodiments described above can be combined in any manner desired dependent upon the operational requirements of the procedure to be performed and the complexity of the rotary tissue cutting instrument. It will also be appreciated that the instrument of the present invention can be used to cut soft and bony tissue in humans and animals.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled rotary tissue cutting instrument comprising an outer blade assembly including a rigid tubular member having proximal and distal portions connected by a bend; and an inner blade assembly rotatably disposed within said outer blade assembly and including a tubular drive shaft at a proximal end, a cutting tip at a distal end, and a flexible coupling disposed between said drive shaft and said cutting tip within said bend in said outer blade assembly;

said flexible coupling including a hollow tubular member formed of a flexible polymeric material and having proximal and distal ends;

said drive shaft and cutting tip including neck portions disposed telescopically within said respective proximal and distal ends of said flexible polymeric coupling, each of said neck portions including a lateral opening defining a predetermined flow path for said polymeric material during fabrication; and said flexible polymeric coupling including inwardly protruding portions molded in place within said openings in said neck portions of said drive shaft and said cutting tip to form permanent, interlocking mechanical joints capable of receiving and transmitting torque.

2. An angled rotary tissue cutting instrument as recited in claim 1 and further comprising a pair of bands formed of shrink wrap tubing disposed around said flexible polymeric coupling adjacent said respective proximal and distal ends of said coupling to provide compressing directing the flow of polymeric material into said openings in said neck portions during fabrication and to provide a pair of lubricious bearing surfaces at opposite ends of said bend during operation.

3. An angled rotary tissue cutting instrument as recited in claim 1 wherein said opening in at least one of said neck portions includes a slot.

4. An angled rotary tissue cutting instrument as recited in claim 3 wherein said slot is defined by laterally opposed edges angled away from one another in the direction of a curved edge connecting terminal ends of said angled edges.

5. An angled rotary tissue cutting instrument as recited in claim 3 wherein said slot is defined by laterally opposed edges angled away from one another in the direction of a straight edge transversely connecting terminal ends of said angled edges.

6. An angled rotary tissue cutting instrument as recited in claim 1 wherein said opening in at least one of said neck portions includes a first slot oriented parallel to a longitudinal axis of said neck portion and a second slot oriented transverse to said first slot.

7. An angled rotary tissue cutting instrument as recited in claim 1 wherein said opening in at least one of said neck portions includes a pair of spaced through-holes.

8. An angled rotary tissue cutting instrument as recited in claim 1 wherein said flexible coupling further includes a plurality of wires embedded within said polymeric tubular member therein as reinforcement.

9. An angled rotary tissue cutting instrument as recited in claim 8 wherein said wires are arranged in a plurality of layers wound in opposite directions to define a mesh-like reinforcing structure within said polymeric coupling.

10. An angled rotary tissue cutting instrument as recited in claim 9 wherein each layer includes a plurality of circumferentially spaced, helically intertwined wires oriented at acute angles relative to the longitudinal axis of said polymeric coupling.

11. An angled rotary tissue cutting instrument as recited in claim 10 wherein said wires are oriented at angles of about 45° relative to said longitudinal axis of said polymeric coupling to transmit torque without substantial preloading.

12. An angled rotary tissue cutting instrument as recited in claim 1 wherein said distal portion of said outer blade assembly is oriented at an angle of between about 35° and about 60° relative to the longitudinal axis of said proximal portion with a bend radius of no more than about 1.5 inches.

13. An angled rotary tissue cutting instrument as recited in claim 12 wherein said bend is located adjacent a distal end of said outer blade.

14. An angled rotary tissue cutting instrument as recited in claim 12 wherein said bend is located adjacent a proximal end of said outer blade.

15. An angled rotary tissue cutting instrument as recited in claim 12 wherein said distal portion of said outer blade defines a cutting window facing outwardly of a center of curvature of said bend.

16. An angled rotary tissue cutting instrument as recited in claim 1 wherein said outer tubular member includes a plurality of bends.

17. An angled rotary tissue cutting instrument as recited in claim 16 wherein said outer tubular member includes a pair of longitudinally spaced bends and an intermediate portion of straight configuration extending between said longitudinally spaced bends.

18. An angled rotary tissue cutting instrument as recited in claim 17 wherein said inner blade assembly includes a pair of flexible couplings disposed in said longitudinally spaced bends and a rigid connecting tube disposed between said flexible couplings.

19. An angled rotary tissue cutting instrument as recited in claim 18 wherein said intermediate portion is oriented at an angle of between about 40° and about 50° in a first direction relative to a longitudinal axis of said proximal portion and said distal portion is oriented at an angel of between about 10° and about 20° in a second, opposite direction relative to a longitudinal axis of said intermediate portion.

20. An angled rotary tissue cutting instrument as recited in claim 19 wherein said said straight portion is oriented at an angle of about 45° relative to a longitudinal axis of said proximal portion and said distal portion is oriented at an angle of about 15° relative to a longitudinal axis of said straight portion.

21. An angled rotary tissue cutting instrument as recited in claim 18 wherein said connecting tube includes a neck portion at each end disposed telescopically within respective ends of said flexible couplings, each of said neck portions including a lateral opening defining a predetermined flow path for said polymeric coupling material during fabrication.

22. A method of fabricating an angled rotary tissue cutting instrument comprising the steps of positioning a neck portion at the proximal end of a cutting tip in the distal end of a flexible polymeric coupling of tubular configuration;

positioning a neck portion at the distal end of a drive shaft in the proximal end of the flexible polymeric coupling;

placing a first band of shrink tubing over a proximal end of the flexible polymeric coupling;

placing a second band of shrink tubing over a distal end of the flexible polymeric coupling;

heating the shrink tubing and the flexible polymeric coupling to cause the polymeric coupling to flow and the shrink tubing to contract around the polymeric coupling such that the polymeric material flows along predetermined flow paths defined by lateral openings in the neck portions of the drive shaft and cutting tip; and cooling the shrink tubing and the flexible polymeric coupling so that flowed portions of the polymeric coupling harden within the openings in the neck portions to form permanent, interlocking mechanical joints therewith capable of receiving and transmitting torque as an integral inner blade assembly.

23. A method of fabricating an angled rotary tissue cutting instrument as recited in claim 22 and further comprising, prior to said heating step, the step of placing a mandrel within the drive shaft and the cutting tip to prevent the polymeric material of the flexible coupling from flowing into the lumen defined by the drive shaft and the cutting tip.

24. A method of fabricating an angled rotary tissue cutting instrument as recited in claim 22 and further comprising, after said heating step, the step of removing the shrink tubing from the polymeric coupling.

25. A method of fabricating an angled rotary tissue cutting instrument as recited in claim 22 and further comprising, after said cooling step, the step of inserting the inner blade assembly within an outer blade assembly including a rigid tubular member having proximal and distal portions connected by a bend.

*26. A rotary tissue cutting instrument forming a laryngeal blade comprising*

*a rigid outer tubular member having a hub, a proximal portion of straight configuration having a longitudinal axis and extending distally from said hub to a proximal bend curving in a first direction, a straight intermediate portion extending distally at an angle to said longitudinal axis of said proximal portion from said proximal bend to a distal bend curving in a second direction opposite to said first direction and a straight distal portion extending distally from said distal bend to a distal end having an opening therein, said proximal portion having a length between said hub and said proximal bend, said intermediate portion having a length between said proximal bend and said distal bend, said distal portion having a length between said distal bend and said distal end and said length of said intermediate portion being greater than said length of said proximal portion and being greater than said length of said distal portion;*

*an inner member rotatably disposed in said outer tubular member and having a proximal end for mounting to a powered handpiece and a distal cutting tip disposed adjacent said opening in said distal end of said outer tubular member, said inner member being flexible adjacent said distal and proximal bends; and*

*a suction passage extending along said inner member to permit aspiration of cut tissue.*

*27. A rotary tissue cutting instrument as recited in claim 26 wherein said length of said proximal portion is about the same as said length of said distal portion.*

*28. A rotary tissue cutting instrument as recited in claim 27 wherein said length of said proximal and distal portions is about 0.5 inch and said length of said intermediate portion is between 8 and 10 inches.*

*29. A rotary tissue cutting instrument as recited in claim 26 wherein said intermediate portion has a longitudinal axis disposed at an angle ranging between about 40° and about 50° relative to said longitudinal axis of said proximal portion and said distal portion is disposed at an angle of about 20° or less relative to said longitudinal axis of said intermediate portion.*

*30. A rotary tissue cutting instrument as recited in claim 29 wherein said angle of said intermediate portion is about 45° and said angle of said distal portion is about 15°.*

*31. A rotary tissue cutting instrument as recited in claim 29 wherein said proximal bend has a radius of curvature of about 1.5 inches and said distal bend has a radius of curvature of about 0.875 inch.*

*32. A rotary cutting instrument as recited in claim 26 wherein said inner member is tubular and said suction passage extends through said inner member.*

*33. A rotary cutting instrument as recited in claim 32 wherein said inner member includes first and second flexible portions extending through said proximal bend and said distal bend, respectively.*

*34. A rotary cutting instrument as recited in claims 32 wherein said inner member includes a drive shaft and a flexible coupling connecting said drive shaft with said distal cutting tip.*

* * * * *